United States Patent [19]

Remy

[11] 4,060,622

[45] Nov. 29, 1977

[54] (+) AND (−) 1-METHYL-4-(3-CYANO-5H-DIBENZO(a,d)-CYCLOHEPTEN-5-YLIDENE)PIPERIDINE CONTAINING COMPOSITIONS AND METHODS FOR USING SAME

[75] Inventor: David C. Remy, North Wales, Pa.

[73] Assignee: Merck & Co., Inc., Rahway, N.J.

[21] Appl. No.: 652,674

[22] Filed: Jan. 27, 1976

Related U.S. Application Data

[63] Continuation of Ser. No. 486,978, July 10, 1974, abandoned.

[51] Int. Cl.$^2$ ............................................ A61K 31/445
[52] U.S. Cl. .............................. 424/267; 260/293.62
[58] Field of Search ..................... 260/293.62; 424/267

[56] References Cited

U.S. PATENT DOCUMENTS

| | | | |
|---|---|---|---|
| 3,511,881 | 5/1970 | Hoffsommer et al. | 260/607 |
| 3,547,980 | 12/1970 | Engelhardt et al. | 260/482 |
| 3,960,872 | 6/1976 | Prugh | 260/293.62 |
| 3,988,342 | 10/1976 | Prugh | 260/293.62 |

FOREIGN PATENT DOCUMENTS

| | | |
|---|---|---|
| 3,558M | 9/1965 | France. |
| 1,046,404 | 10/1966 | United Kingdom. |

OTHER PUBLICATIONS

Ebnöther et al., Helv. Chim. Acta. 1965, vol. 48, pp. 1237–1249.

*Primary Examiner*—Natalie Trousof
*Attorney, Agent, or Firm*—William H. Nicholson; Harry E. Westlake, Jr.

[57] ABSTRACT

Resolution of 1-methyl-4-(3-cyano-5H-dibenzo-[a,d]-cyclohepten-5-ylidene)piperidine provides a levorotary isomer (−) having major tranquilizer pharmaceutical utility and a dextrorotary isomer (+) having anticholinergic pharmaceutical utility. Also disclosed are pharmaceutical compositions comprising either isomer substantially free of the other; pharmaceutical compositions comprising preferred ratios of the (+) and (−) isomers; and methods of treatment comprising administering such compounds and compositions.

4 Claims, No Drawings

(+) AND (−) 1-METHYL-4-(3-CYANO-5H-DIBENZO(A,D)-CYCLOHEPTEN-5-YLIDENE)PIPERIDINE CONTAINING COMPOSITIONS AND METHODS FOR USING SAME

This is a continuation, of application Ser. No. 486,978 filed July 10, 1974 (now abandoned).

BACKGROUND OF THE INVENTION

This invention relates to (+) 1-methyl-4-(3-cyano-5H-dibenzo[a,d]-cyclohepten-5-ylidene)piperidine (hereinafter referred to as "(+) 3-cyanocyproheptadine") having pharmaceutical utility as a peripheral and central anticholinergic agent; and to (−) 1-methyl-4-(3-cyano-5H-dibenzo[a,d]-cyclohepten-5-ylidene)piperidine (hereinafter referred to as "(−) 3-cyanocyproheptadine") having pharmaceutical utility as a major tranquilizer. Further this invention relates to a process for resolving racemic 3-cyanocyproheptadine into (−) 3-cyanocyproheptadine and (+) 3-cyanocyproheptadine; to pharmaceutical compositions comprising either isomer substantially free of the other; pharmaceutical compositions comprising preferred ratios of the (+) and (−) isomers; and to methods of treatment comprising administering such compounds and compositions.

The symbols, "(+)" and "(−)," as used above, indicate that under the conditions of measurement hereinafter described, e.g., frequency, temperature and solvent, the subject compounds rotate the plane of polarized light to the right or left, respectively, when viewed according to the established convention. For purposes of this invention the phrase "substantially free" when referring to the state of purity of one isomer with respect to its enantiomer is defined to be a contamination of the pure isomer by from about 0.1 to about 5.0 wt. % of its enantiomer.

The racemic 3-cyanocyproheptadine (structure I, below) has been disclosed in commonly assigned, co-pending U.S. Pat. application Ser. No. 476,630, filed June, 5, 1974 of John D. Prugh, now U.S. Pat. No. 3,988,342, which application is a continuation-in-part of Ser. No. 280,685, filed Aug. 14, 1972, now U.S. Pat. No. 3,960,872, which in turn is a continuation-in-part of U.S. Ser. No. 9,049, filed Feb. 5, 1970, now abandoned, which in turn is a continuation-in-part of U.S. Ser. No. 4,123, filed Jan. 19, 1970, now abandoned. For the purpose of describing the synthesis of the racemic 3-cyanocyproheptadine, such applications are incorporated herein by reference.

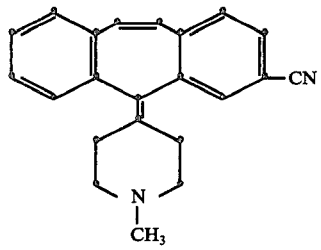

I

However, there is no disclosure in the above-mentioned U.S. patent applications that resolution of the racemic 3-cyanocyproheptadine also effects a separation of pharmacological activity. Thus while the racemic 3-cyanocyproheptadine is a potent major tranquilizer it also has potent anticholinergic activity which latter activity can give rise to undesired side effects; the (+) isomer, however, has no tranquilizing activity but is a potent peripheral and central anticholinergic agent and can be used as an anticholinergic agent or for treatment of the extrapyramidal effects of haloperidol and similar agents; whereas the (−) isomer has no central or peripheral anticholinergic activity but is a major tranquilizer. The unexpected separation of pharmacological activity by optical resolution of the racemic 3-cyanocyproheptadine into its enantiomer is of significant value since it is now possible to obtain either tranquilizing effects, anticholinergic effects or a desired combination of such effects by administering either isomer substantially free of its enantiomer or by administering a combination of the isomers in preferred ratios.

Thus it is an object of the present invention to provide (+) 3-cyanocyproheptadine substantially free of the corresponding (−) enantiomer; (−) 3-cyanocyproheptadine substantially free of the corresponding (+) enantiomer; and preferred ratios of the two isomers. It is also an object of the present invention to provide processes for the preparation (resolution) of such optical isomers from the racemic mixture.

A further object of this invention is to provide pharmaceutical compositions comprising therapeutically effective amounts of such isomers substantially free of the corresponding enantiomer and compositions comprising therapeutically effective amounts of preferred blends of such isomers. Further it is an object of the present invention to provide methods of treatment comprising administering such compounds and compositions when the effects of a major tranquilizer, anticholinergic agent, or a combination of said effects is indicated.

Lastly, it is an object of the present invention to provide pharmaceutically acceptable acid addition salts of the above-described compounds.

DETAILED DESCRIPTION OF THE INVENTION

The racemic 3-cyanocyproheptadine may conveniently be prepared from the corresponding 3-bromocyproheptadine which is disclosed in U.S. Pat. No. 3,014,911, Dec. 26, 1961 (incorporated herein by reference) according to the following reaction:

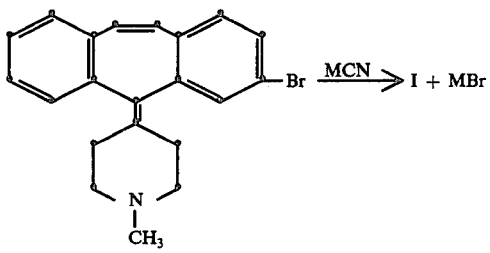

wherein the 3-bromocyproheptadine is treated with a metal cyanide (MCN) such as cuprous cyanide or the like in an inert solvent medium such as N,N-dimethylformamide, N-methylpyrrolidone, and the like at a temperature of from about 80° to about 180° C.

The preferred method of resolution of the racemic 3-cyanocyproheptadine to provide (−) 3-cyanocyproheptadine substantially free of the (+) enantiomer and (+) 3-cyanocyproheptadine substantially free of the (−) enantiomer comprises forming diastereomeric salts of racemic 3-cyanocyproheptadine with optically active acids such as di-p-toluoyl-d-tartaric acid, di-p-toluoyl-l-tartaric acid, l-malic acid, and the like, in a suitable solvent such as methanol, ethanol, 2-propanol, benzene, acetonitrile, nitromethane, acetone, and the like. In principle the diasteriomeric salts formed from solution differ in physico-chemical properties such that one salt may be separated from the other, i.e., differences in solubility. Repetitive recrystallizations afford a substantially pure diastereomer, which upon treatment with base such as sodium bicarbonate, sodium carbonate, sodium hydroxide and the like; extraction into a nonpolar or semipolar solvent such as ether, benzene, chloroform, and the like; followed by evaporation of the solvent and recrystallization yields one enantiomer substantially free of the other. Ideally, the other enantiomer is obtained from the supernatant solution following removal of the first precipitated diasteriomer in comparable purity by evaporation, conversion to the free base form, and recrystallization.

In the method of treatment and pharmaceutical composition aspects of the present invention, it is to be noted that the precise unit dosage form and dosage level depend upon the case history of the individual being treated and consequently are left to the discretion of the skilled therapist. In general, however, the compounds of the present invention and preferred combinations thereof may be administered to persons in any of the usual pharmaceutical oral forms such as tablets, elixirs and aqueous suspensions in an amount of from about 0.05 to about 500 mg. per dose given two to four times daily. Sterile solutions for injection containing from about 0.025 to about 250 mg. per dose are injected two to four times daily. Further, the compounds of this invention are ordinarily easily administered as a salt and any convenient nontoxic acid addition salt formed in a conventional manner may be employed. Examples of such salts include: the hydrochloride, sulfate, phosphate, acetate, propionate, citrate, tartrate, succinate, and the like. These salts are generally equivalent in potency to the base from which they are formed taking into consideration the stoichiometric quantities employed.

The following examples representatively illustrate but do not limit the product, compositional, method of resolution, or method of treatment aspects of the present invention.

EXAMPLE 1

Resolution of (±) 1-methyl-4-(3-cyano-5H-dibenzo[a,d]-cyclohepten-5-ylidene)piperidine To a solution of 4.37 g. (0.014 mole) of (±) 1-methyl-4-(3-cyano-5H-dibenzo[a,d]cyclohepten-5-ylidene)-piperidine in 20 ml. of ethanol at 25° C. is added 5.40 g. (0.014 mole) of di-p-toluoyl-d-tartaric acid. The crystalline precipitate that forms on cooling is removed by filtration, washed with cold ethanol, and dried at 100° C. in vacuo to give 6.75 g. of material, designated A. The clear ethanol filtrate and washings are designated B.

The 6.75 g. of A is recrystallized from absolute ethanol six times to give a product that has a constant rotation, m.p. 169.5°–171.5°; $[\alpha]_{589}^{25} = -142°$, $[\alpha]_{578}^{25} = -150°$, $[\alpha]_{546}^{25} = -180°$, $[\alpha]_{436}^{25} = -434°$, (C = 0.010 g./ml. pyridine). This material is dissolved in the minimum amount of water and a 1.0 M aqueous sodium bicarbonate solution is added dropwise to complete precipitation. The resulting precipitate is extracted into chloroform, washed with water, and dried over magnesium sulfate. After filtering, the chloroform is evaporated. The residue is triturated with acetonitrile, collected by filtration and dried at 100° C. in vacuo to give (−) 1-methyl-4-(3-cyano-5H-dibenzo[a,d]cyclohepten-5-ylidene)piperidine, m.p. 176°–178°; $[\alpha]_{589}^{25} = -191°$, $[\alpha]_{578}^{25} = -202°$, $[\alpha]_{546}^{25} = -248°$, $[\alpha]_{436}^{25} = -671°$, (C = 0.010 g./ml. CHCl$_3$).

Elemental analysis for $C_{22}H_{20}N_2$.
Calc.: C, 84.58; H, 6.45; N, 8.97.
Found: C, 84.32; H, 6.52; N, 9.00.

The ethanol filtrate and washings, B, are allowed to stand at room temperature for 7 days. The supernatant liquid is decanted from a small amount of crystalline material. This supernatent liquid is allowed to stand 7 days at room temperature, after which time it is decanted again. The ethanol is removed by evaporation. The residue is dissolved in the minimum amount of water and treated with an aqueous solution of sodium bicarbonate to achieve an alkaline pH. The resulting precipitate is extracted into chloroform, washed with water, and dried over magnesium sulfate. After filtering, the chloroform is evaporated. The residue is recrystallized three times from acetonitrile, collected and dried at 100° C. in vacuo to give (+) 1-methyl-4-(3-cyano-5H-dibenzo[a,d]cyclohepten-5-ylidene, m.p. 177.5°–179.5°; $[\alpha]_{589}^{25} = +191°$, $[\alpha]_{578}^{25} = +205$, $[\alpha]_{546}^{25} = +250°$, $[\alpha]_{436}^{25} = +675°$, (C = 0.010 g./ml. CHCl$_3$).

Elemental analysis for $C_{22}H_{20}N_2$:
Calc.: C, 84.58; H, 6.45; N, 8.97.
Found: C, 84.50; H, 6.62; N, 8.74.

EXAMPLE 2

Pharmaceutical compositions

A typical tablet containing 1 mg. of (+) 1-methyl-4-(3-cyano-5H-dibenzo[a,d]-cyclohepten-5-ylidene)-piperidine per tablet is prepared by mixing together with the active ingredient calcium phosphate, lactose and starch in the amounts shown in the table below. After these ingredients are thoroughly mixed, the appropriate amount of magnesium stearate is added and the dry mixture blended for an additional three minutes. This mixture is then compressed into tablets weighing approximately 124 mg. each.

| TABLET FORMULA | |
|---|---|
| INGREDIENT | MG. PER TABLET |
| (+) 1-methyl-4-(3-cyano-5H-dibenzo-[a,d]-cyclohepten-5-ylidene)-piperidine | 1 mg. |
| Calcium phosphate | 52 mg. |
| Lactose | 60 mg. |
| Starch | 10 mg. |
| Magnesium stearate | 1 mg. |

In a similar manner tablets comprising (−) 1-methyl-4-(3-cyano-5H-dibenzo[a,d]cyanohepten-5-ylidene)-piperidine are prepared according to the procedure of Example 2 when the (+) 3-cyanocyproheptadine is replaced by an equivalent amount of (−) 3-cyanocyproheptadine. Similarly prepared are tablets comprising a preferred blend for a specific purpose of the optical isomers, (+) and (−) 3-cyanocyproheptadine; the following tablet formula is illustrative of such blends:

| TABLET FORMULA | |
|---|---|
| INGREDIENT | MG. PER TABLET |
| (+) 1-methyl-4-(3-cyano-5H-dibenzo-[a,d]-cyclohepten-5-ylidene)-piperidine | 0.10 mg. |
| (−) 1-methyl-4-(3-cyano-5H-dibenzo[a,d]-cyclohepten-5-ylidene)-piperidine | 0.90 mg. |
| Calcium phosphate | 52 mg. |
| Lactose | 60 mg. |
| Starch | 10 mg. |
| Magnesium stearate | 1 mg. |

What is claimed is:

1. A method of producing a tranquilizing effect comprising administering to a patient in need of such treatment a therapeutically effective amount of (−) 1-methyl-4-(3-cyano-5H-dibenzo[a,d]-cyclohepten-5-ylidene)-piperidine substantially free of the corresponding dextrorotary isomer or a nontoxic pharmaceutically acceptable acid addition salt thereof.

2. A method of producing an anticholinergic effect comprising administering to a patient in need of such treatment a therapeutically effective amount of (+) 1-methyl-4-(3-cyano-5H-dibenzo[a,d]-cyclohepten-5-ylidene)-piperidine substantially free of the corresponding levorotary isomer or a nontoxic pharmaceutically acceptable acid addition salt thereof.

3. A pharmaceutical composition in unit dosage form comprising a therapeutically effective amount of (−) 1-methyl-4-(3-cyano-5H-dibenzo[a,d]-cyclohepten-5-ylidene)-piperidine substantially free of the corresponding dextrorotary isomer or a nontoxic pharmaceutical acid addition salt thereof and a pharmaceutical carrier therefor.

4. A pharmaceutical composition in unit dosage form comprising a therapeutically effective amount of (+) 1-methyl-4-(3-cyano-5H-dibenzo[a,d]-cyclohepten-5-ylidene)-piperidine substantially free of the corresponding levorotary isomer or a nontoxic pharmaceutical acid addition salt thereof and a pharmaceutical carrier therefor.

* * * * *